US006921438B2

(12) United States Patent
Lausevic

(10) Patent No.: US 6,921,438 B2
(45) Date of Patent: Jul. 26, 2005

(54) VACUUM CLEANER ATTACHMENT FOR FUNGI REMOVAL AND METHOD OF USE THEREOF

(76) Inventor: John Lausevic, Pacific Gold Coast Construction, Inc., 3107 Pico Blvd., Suite K, Santa Monica, CA (US) 90405

( * ) Notice: Subject to any disclaimer, the term of this patent is extended or adjusted under 35 U.S.C. 154(b) by 444 days.

(21) Appl. No.: 10/208,578

(22) Filed: Jul. 30, 2002

(65) Prior Publication Data

US 2004/0020007 A1 Feb. 5, 2004

(51) Int. Cl.$^7$ .......................... A47L 9/06; B24D 15/04; B24B 55/06
(52) U.S. Cl. .......................... 134/21; 15/393; 15/415.1; 15/420; 134/6; 451/456; 451/524; 451/525
(58) Field of Search .......................... 15/393, 401, 402, 15/415.1, 420; 134/6, 21; 451/344, 456, 523, 524, 525

(56) References Cited

U.S. PATENT DOCUMENTS

| | | | | |
|---|---|---|---|---|
| 1,296,121 | A | * 3/1919 | Rosenfield | 15/393 |
| D152,589 | S | 2/1949 | Burri | |
| 2,499,933 | A | * 3/1950 | Smul | 451/522 |
| 2,893,048 | A | * 7/1959 | Martinec | 15/422 |
| 2,934,780 | A | * 5/1960 | Taplin | 15/402 |
| 3,512,208 | A | * 5/1970 | Spencer | 15/368 |
| 4,677,705 | A | * 7/1987 | Schuster | 15/398 |
| 4,680,895 | A | 7/1987 | Roestenberg | |
| 4,694,529 | A | * 9/1987 | Choiniere | 15/393 |
| 4,759,155 | A | 7/1988 | Shaw | |
| 4,779,385 | A | 10/1988 | Reiter | |
| 4,937,984 | A | * 7/1990 | Taranto | 451/524 |
| 5,036,627 | A | * 8/1991 | Walters | 451/354 |
| 5,283,988 | A | * 2/1994 | Brown | 451/524 |
| 5,297,363 | A | 3/1994 | Schroder et al. | |
| 5,527,212 | A | * 6/1996 | Bowen et al. | 451/456 |
| 5,533,230 | A | * 7/1996 | Rouda | 15/339 |
| 5,634,843 | A | 6/1997 | Liu | 451/344 |
| 6,053,805 | A | * 4/2000 | Sanchez | 451/456 |
| 6,421,875 | B1 | * 7/2002 | Coombs et al. | 15/420 |

FOREIGN PATENT DOCUMENTS

WO  WO 93/01913  2/1993

* cited by examiner

Primary Examiner—Terrence R. Till
(74) Attorney, Agent, or Firm—Cislo & Thomas LLP

(57) ABSTRACT

A vacuum cleaner attachment and method of use thereof provides an effective cleaning system for fungi and the like. A vacuum paddle extension enables the attachment to travel into narrow cracks and crevices where fungus may grow and by use of an abrasive and porous pad dislodges such fungus or fungi. When attached to a vacuum system, such as a HEPA (High Efficiency Particulate Air-Filtered) vacuum system, the debris and particulate matter generated by the abrasive process is drawn into the vacuum attachment and into the vacuum system where it is removed from the air which is then expelled by the vacuum system. Better cleaning of surfaces afflicted with fungi, molds, and the like is then achieved in a manner that is safer and more effective.

16 Claims, 3 Drawing Sheets

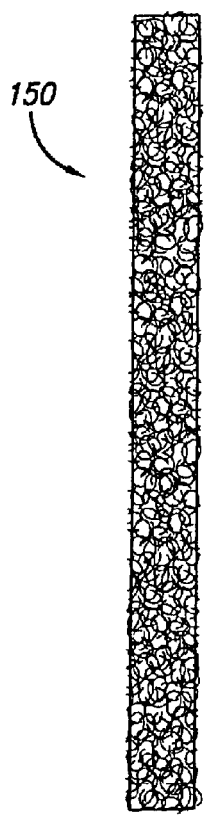
FIG. 3
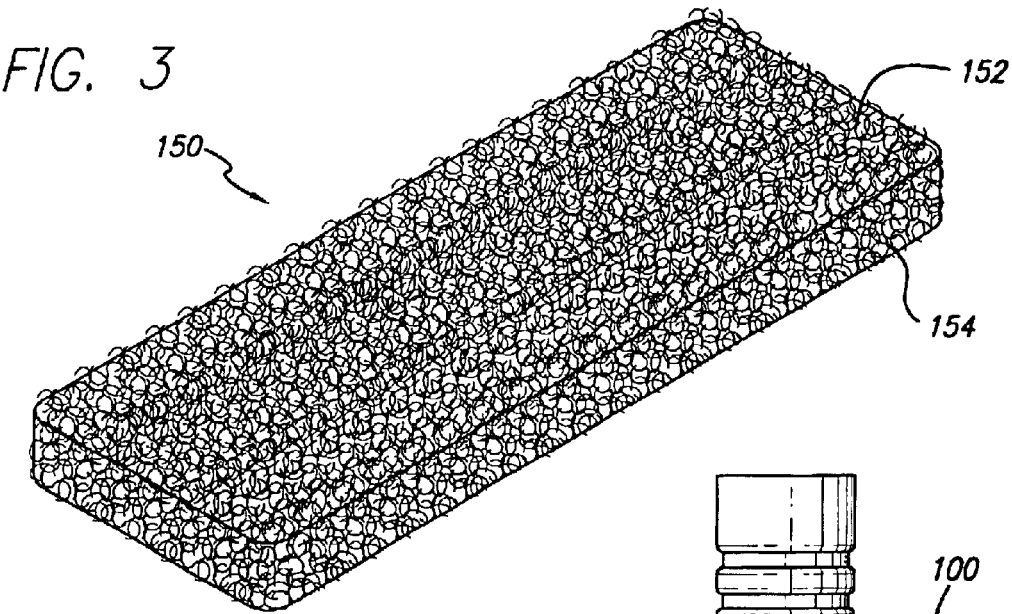
FIG. 4
FIG. 5
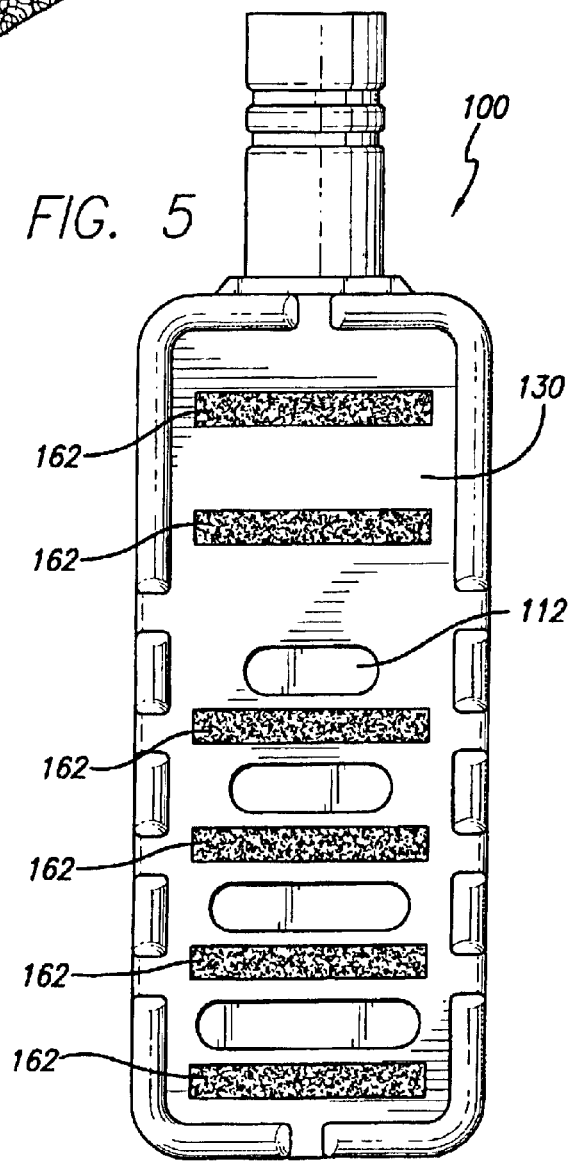

VACUUM CLEANER ATTACHMENT FOR FUNGI REMOVAL AND METHOD OF USE THEREOF

BACKGROUND OF THE INVENTION

1. Field of the Invention

This invention relates to biological cleaning procedures and apparatus and more particularly to a vacuum cleaning attachment that enables better fungus removal and the process therefore.

2. Description of the Related Art

With advanced techniques in buildings, homes and offices, the interior space defined by the structure is often well-sealed from the outside environment. While this provides significant protection against the ambient environment, it also locks in the local environment from consistent aeration. A classic example of this is when the Astrodome in Houston, Tex. was originally constructed, condensation would collect to such an extent that it would periodically rain inside the Astrodome. While such precipitation may be very minor in nature, it does indicate the possibility of microclimates being defined within structures.

With such structures, it is possible that fungus can grow on interior surfaces, inside the walls, or the like. This sometimes gives rise to a phenomenon known as "sick building" syndrome. People inside the building sometimes fall ill on a basis that is higher than that statistically predictable. More people get sick than what is expected. Over time, air conditioning ducts, vents, and the like may collect condensation or certain structures within the building become a host to fungus, mold, or other organisms.

Furthermore, flooding, water damage, and the like can give rise to fungi and/or mold if (for example) wooden studs within the building get soaked or there is otherwise an opportunity for parasitic fungi and mold to find and exploit a host structure.

While such processes are natural in nature (such fungi and molds are merely reclaiming dead wood in a saprophytic nature or otherwise), they can often be to the detriment of the individual's working or living in adjacent environments. Such fungi and allergens, toxins, or irritants can cause illness. Furthermore, if such fungi and molds can use human beings, other mammals, or other animals as hosts, the fungi and mold can spread to such animals. Such diseases may be difficult to treat and/or heal. Furthermore, the environment created by fungi and molds may give rise to other bacteria or microbiological agents that can detrimentally affect people or their living space.

Certain attempts have been made in the prior art to address such conditions. These include:

U.S. Pat. No. 2,499,933 to Smul pertains to an attachment of the type for removing paint, varnish, etc., wherein the attachment is adapted to be connected to a vacuum source. The attachment is somewhat elongated or paddle-shaped and has a plurality of apertures therethrough with an abrasive cloth or sandpaper configured to cover the face of member 25.

PCT Publication WO 93/01913 to Galassi, et al. relates to a pad of flexible and resilient material for hand smoothing surfaces by abrasive paper and includes a fluid passageway or communication that is adapted to be connected to a vacuum source. The replaceable abrasive paper 4 is formed with corresponding holes 5'. While Velcro is mentioned, it is to make the handle 10 of an adjustable nature.

U.S. Pat. No. 5,634,843 to Liu relates to a multi-functional, grinding wiper which discloses a removable emery sheet 10 with a plurality of apertures. One embodiment speaks to self adhesive tape for adhering an abrasive surface in the assemblage. See column 3, line 10, et seq. of the patent.

U.S. Pat. No. 4,779,385 to Reiter relates to a gypsum board sanding device which is adapted to be coupled to a vacuum cleaner and is significant with respect to its overall general showing of a vacuum attachment having a plurality of holes therethrough and wherein the same is adapted to support a perforated sheet S of sandpaper mounted thereon which is held in place by means of a spring loaded clamp 60 but it also contemplates that the sandpaper S can be adhesive-backed for direct affixation to the top surfaces of the pedestals 52 and 54.

Design Patent No. 152,589 to Burri is quite dissimilar in configuration to the paddle-shaped attachment that is manifest in the present invention.

Despite these prior attempts, the technology available to scrub or abrade structures in order to rid them of mold, fungi, and the like by using a vacuum system or otherwise is not one that is fully developed and one in which further development can be advantageously made to the benefit of the afflicted public. The present invention solves a current problem, namely inadequate or inefficient mold and fungi-removal process, as well as contributing to the art by providing additional advance in providing such efficient and increasing the ability to remove fungi and mold from afflicted structure and structure element.

SUMMARY OF THE INVENTION

In view of the foregoing disadvantages inherent in the known types of fungus and mold-removing tools now present in the prior art, the present invention provides a vacuum cleaner attachment for fungi removal and method of use thereof wherein fungi, mold, and other particulate matter that adheres to structure elements and is removed by gentle abrasion is effected generally in conjunction with a HEPA (High Efficiency Particulate Air Filter) vacuum.

The general purpose of the present invention, which is described subsequently in greater detail, is to provide such a vacuum cleaner attachment and method in order to provide better removal of fungi, mold, and other surface agents that are attached to building or office structure elements or furnishings (soft goods, upholstered walls or furniture), which is not anticipated, rendered obvious, suggested, or even implied by any of the prior art tools, either alone or in any combination thereof.

Using a narrow and projecting vacuum paddle, the vacuum cleaner attachment of the present invention provides better means by which fungus can be removed from structural elements. Using a long narrow paddle, surface areas are better addressed and engaged by the vacuum cleaner attachment of the present invention. The high efficiency vacuum collects the loosened or freed particles created by the abrasion of the vacuum cleaner attachment with the underlying fungi-infected surface.

In order to provide an abrasive surface, scrub pad or the like is removably adhered to the underside of the vacuum paddle. This pad provides the abrasion of the building surface from which fungus is to be removed. The underside of the vacuum paddle has a series of holes which may have greater cross section as travel is made away from attachment of the vacuum cleaner at its proximal end to its distal end. This enables better balancing of air flow so that the narrow hole near the vacuum source pulls in approximately the same volume of air as the wider hole farther away. Ridges may circumscribe the perimeter of the underside of the vacuum paddle and may have valleys or slots through which air can travel. It is best to have a large volume of air travel through the vacuum paddle in order to remove as much particulate or aerosolized dust and fungus as possible. However, with such a high amount of air flow, the paddle could adhere to the surface by means of vacuum pressure. The ridges hold the vacuum paddle above surface below it and the slots between the ridges allow the vacuum to be broken so that the vacuum attachment may be lifted from the surface should it come into contact with it.

The abrasive pad may be adhered to the underside of the vacuum paddle by means of VELCRO® or other hook fastener. Other removable means, such as adhesive or the like, may also be used to attach the abrasive pad to the underside of the vacuum paddle. Once the vacuum paddle is in place and the vacuum source is engaged, air flows through the porous pad into the vacuum cleaning system. The surface to clean is then abraded by the pad and material loosened by such abrasion is then pulled into the vacuum cleaner via the vacuum paddle and the apertures.

OBJECTS OF THE INVENTION

It is an object of the present invention to provide a better system by which fungus may be removed from building structures and the like.

It is another object of the present invention to provide a vacuum cleaner attachment that better cleans fungal spores from fabric upholstered goods.

It is another object of the present invention to provide a vacuum cleaner attachment that uses a disposable scrub pad.

It is another object of the present invention to provide a vacuum cleaner attachment for the removal of fungus growth from sheet metal duct surfaces located in building structures.

It is yet another object of the present invention to provide a method by which fungus may be better removed from building structures.

It is yet another object of the present invention to provide a vacuum cleaner attachment for the removal of fungus or the like that uses disposable pad.

These and other objects and advantages of the present invention will be apparent from a review of the following specification and accompanying drawings.

BRIEF DESCRIPTION OF THE DRAWINGS

FIG. 3 is a front left top and perspective view of an abrasive and porous pad for use in conjunction with the vacuum cleaner attachment.

FIG. 4 is a left side elevational view of the porous abrasive pad shown in FIG. 3.

FIG. 5 is a bottom plan view of the vacuum cleaner attachment similar to that shown in FIG. 2 with the addition of strips for removably adhering an abrasive scrubbing pad such as that shown in FIGS. 3 and 4.

DESCRIPTION OF THE PREFERRED EMBODIMENT(S)

The detailed description set forth below in connection with the appended drawings is intended as a description of presently-preferred embodiments of the invention and is not intended to represent the only forms in which the present invention may be constructed and/or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

Preliminarily, as used herein, the term "fungus" is used to indicate not only fungi, but any surface contaminate that is susceptible to cleaning by the present invention, including mold, mildew, asbestos, lead paint, dusts and other particulate matter, etc.

The present invention provides efficient useful means by which fungus can be removed from building structure including wood or metal studs that are subject to mold growth.

Figure 1:
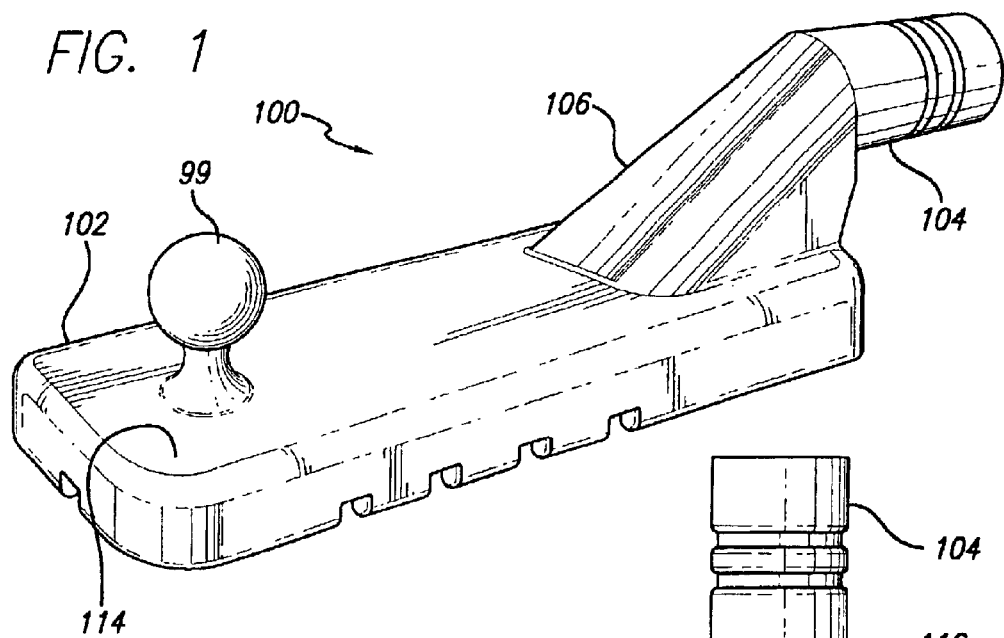
FIG. 1 is a left front and top perspective view of one embodiment of the vacuum cleaner attachment of the present invention showing an upraised protuberance.

As shown in FIG. 1, one embodiment of the vacuum cleaner attachment 100 of the present invention has an extending flat paddle portion 102 and a projecting connector mediated by a transition cowling 106. The entirety of the vacuum cleaner attachment 100 may be referred to here as the vacuum paddle 100 or by similar term.

Figure 2:
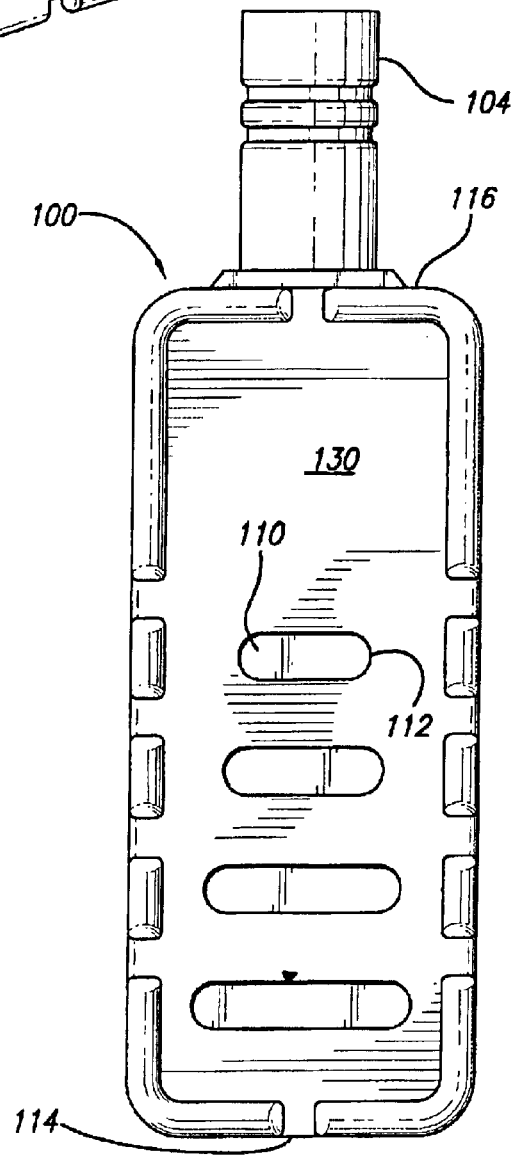
FIG. 2 is a plan view of the underside of the vacuum cleaner attachment shown in FIG. 1.
Figure 6:
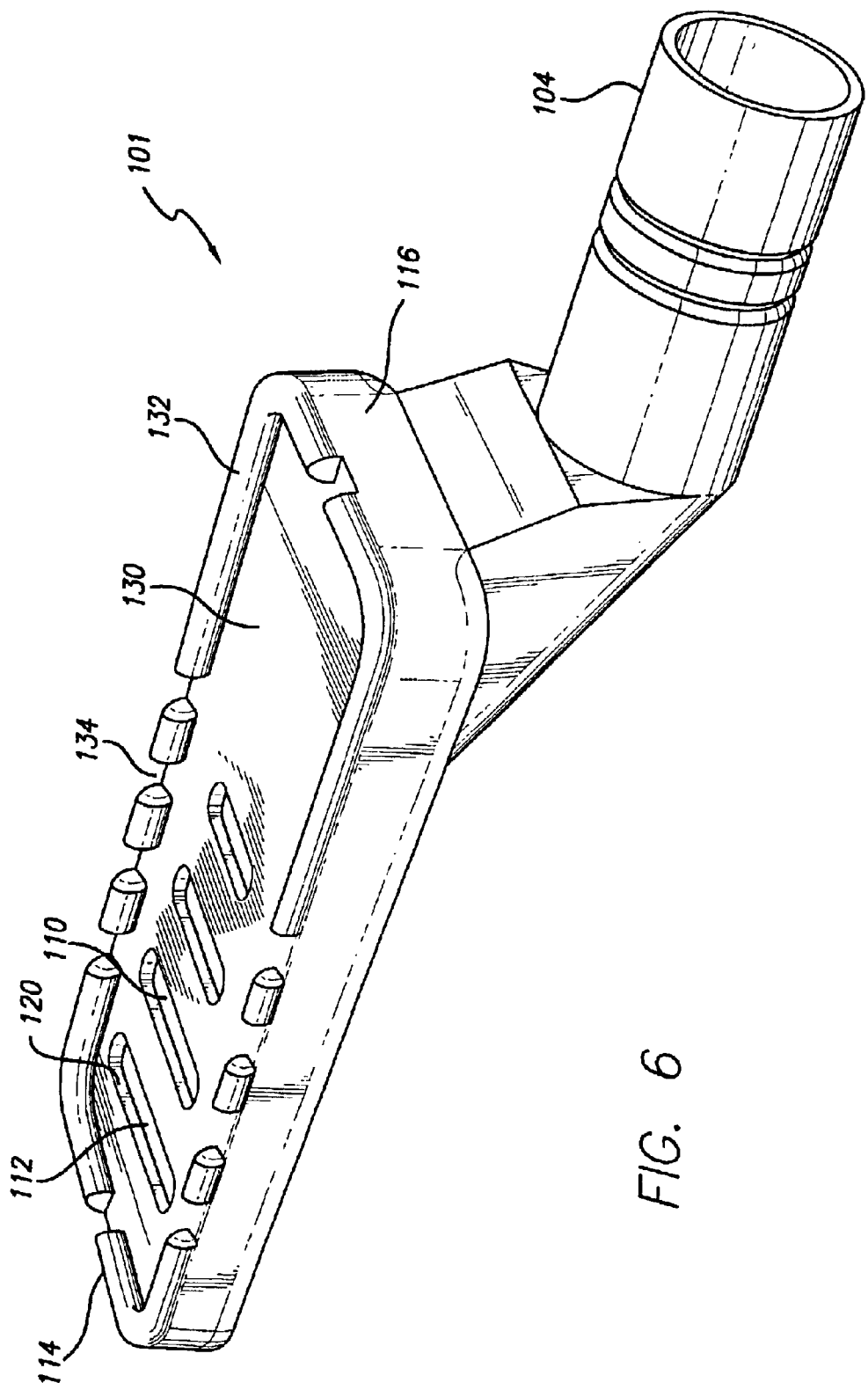
FIG. 6 is a right rear perspective view of another embodiment of the vacuum cleaner attachment of the invention, but without the upraised protuberance and particularly indicating ridges and valleys therebetween as well as the intruding walls circumscribing the apertures that would also be applicable to the FIG. 1 embodiment.

The vacuum cleaner attachment 100 defines an interior plenum 110 inside the extending flat paddle 102. This interior plenum 110 is in communication with the hollow interior of the mediating plenum defined by the transition cowling 106 which then leads into the hollow center airway of the projecting connector 104. Apertures 112 allow the air to flow into the plenum 110 and as indicated in FIGS. 2, 5, and 6, the apertures increase in cross section as travel is made to the distal end 114 away from the proximal end 116 of the paddle portion 102. Additionally, as especially shown in FIG. 6, intruding walls 120 are present that may circumscribe each of the apertures and force any air flowing there through to pass further into the interior plenum 110 before proceeding out the connector 104.

Circumscribing the bottom panel 130 of the vacuum attachment 100 are a series of ridges 132 defining valleys or slots 134 there between on an intermittent basis. The ridges 132 prevent the flat bottom panel 130 from adhering to a surface by vacuum pressure should the face of the bottom panel 130 come into contact with such a flat surface. The ridges 132 hold the bottom panel 130 above the surface while the slots 134 enable air to flow into the apertures 112 so that a pressure difference is present between the interior plenum 110 and the area outside the ridges 132 but such pressure difference is not sufficient to cause the bottom panel 130 to adhere to the flat surface and consequently the entire vacuum paddle attachment 100 to adhere to the same surface by vacuum pressure.

As shown in Figures the slots 134 are distributed around the bottom panel 130 at the front distal end 114, the rear proximal end 160 and generally on either side of the apertures 112. This focuses the flow of air onto the apertures so that more fungal dust or particulate matter, etc. is collected therethrough.

As shown in FIGS. 3 and 4, an abrasive pad 150 has an abrasive and porous outer surface 152 with a supporting under surface 154. The side view of FIG. 4 shows that undersurface 154 has a plurality of undulating peaks and valleys made up of the porous and abrasive natural or synthetic material such that the undersurface 154 acts much like the loop portion of a Velcro fastener by which the pad 150 is releasably secured to the undersurface or flat bottom panel 130 of vacuum attachment 100. Strips 162 in this instance are corresponding hook portions of a hook and loop fastener system. Other gripping means may be used to obtain a temporary or releasable mechanical attachment. Alternatively, a temporary or releasable adhesive may be used on the abrasive pad 150 to temporarily and releasably adhere the underside of the supporting surface 154 to the bottom panel 130. Other means as are known in the art or developed in the future may also be used temporarily and removably, but stably, adhere the abrasive pad 150 to the bottom, panel 130 of the vacuum panel attachment 100.

Once the abrasive pad 150 has been releasably affixed to the vacuum attachment 100, the accompanying vacuum system may be engaged in order to create air flow through the apertures 112. A surface to be cleaned may then be rubbed by the abrasive pad 150 in order to dislodge fungus or other matter from the surface of the structure. The abrasive surface 152 of the abrasive pad 150 may be designed for particular uses and may have a degree of abrasion that is appropriate for the task at hand. A coarse abrasive surface may be used for CMU block and the like while a much finer abrasive surface may be used for fine wood or cellulose backed building materials.

The abrasive pad 150 is sufficiently porous and coarse to allow air to flow there through. The pad material may be natural or synthetic material and the abrasiveness will be selected for the clearing task at hand.

A suitable pad and material that has been found suitable are those sold under SCOTCH-BRITE® trademark of the 3M company. These pads are made of 3-dimensional, non-woven nylon webs impregnated with abrasive materials and bonded together with cured resinous binders. Pad materials may be fine or course depending upon the surface to be worked upon. An ideal pad is one designated by 3M as a light duty cleaning pad 7445.

Obviously other fibers and materials will suggest themselves to those of ordinary skill in the art, the only requirement being that the pad is porous and made of material that will accomplish the desired result of mold, etc. removal with as little surface damage as possible.

Generally, a forward and back motion is used parallel to the axis between the proximal 116 and distal 114 ends of the bottom panel 130. This generally prevents inefficiencies and allows more of the dislodged particulate matter to be drawn into the vacuum attachment 100 while diminishing aerosolization of the resulting dust.

Preferably, that attached vacuum system is an industrial HEPA vacuum system. The HEPA system is a high efficiency particulate air-filtered system that is used to remove fine particles from matter drawn into the vacuum system. Additionally, duct tape or other supplemental adhesive fabric tape may be used in an alternative embodiment to secure a vacuum hose to the projecting connector 104. The duct tape will generally act as a temporary but very effective adhesion system enabling the vacuum attachment 100 to be used in a rough and robust manner.

Use of the abrasive pad 150 will, over time, embed part of the underlying abraded surface into the abrasive fibers of the abrasive pad 150. Over time, the effectiveness of the abrasive pad 150 will diminish and at some point it becomes effective to remove and discard the abrasive pad. The pad can be HEPA vacuumed and rotated if effectiveness is diminished. The abrasive pad 150 should be discarded as a contaminant in an appropriately-sealed container so that the matter dislodged from the underlying building structure may not be cross-contaminated or transmitted to others or into the air. In the alternative embodiment of FIG. 1, a knob, handle or protuberance 99 may be placed near the distal end 114 of the extending flat panel portion 102 of the attachment 100. This would allow two hands to be used in order to enhance the abrasive process to dislodge the particulate matter from the underlying surface. It would also better distribute and distribute more pressure from the person using the attachment 100 in order to make quicker work of the cleaning task at hand.

While the present invention has been described with regards to particular embodiments, it is recognized that additional variations of the present invention may be devised without departing from the inventive concept, such as locating the hollow projecting transition cowling to the center of the paddle device and re-arranging the aperture openings into the interior plenum.

What is claimed is:

1. An attachment for a vacuum cleaning system, comprising:
   a vacuum paddle attachable to a vacuum system at a point of attachment, said vacuum paddle defining paddle apertures through which air may flow, said vacuum paddle defining an interior plenum space coupled to said paddle apertures; said vacuum paddle undersurface being adapted to releasably retain a porous abrasive pad,
   said vacuum paddle having a generally flat and narrow forward projection for reaching away from said point of attachment and enabling said vacuum paddle to reach into narrow areas; and
   circumscribing ridges circumscribing said paddle apertures and defining valley openings through which air may flow when said vacuum paddle is placed against a flat surface to ensure air flow to said paddle apertures and to prevent said vacuum paddle from becoming attached to said flat surface by vacuum pressure; a porous abrasive pad releasably secured to the undersurface of said vacuum paddle whereby
   said vacuum paddle enables better vacuuming of very fine particles.

2. An attachment for a vacuum cleaning system as set forth in claim 1, wherein said point of attachment further comprises:
   a hollow projection defining an airway and coupleable to the vacuum cleaning system.

3. An attachment for a vacuum cleaning system as set forth in claim 2, further comprising:
   said vacuum paddle generally defining a plane; and
   said hollow projection being generally parallel to but offset from said plane.

4. An attachment for a vacuum cleaning system as set forth in claim 2, further comprising:
   a transition cowling defining a mediating plenum coupled on a first side to said vacuum paddle and on a second side to said projection, said mediating plenum in communication with said interior plenum and said airway, said mediating plenum having a larger cross-section nearer said interior plenum and having a narrower cross-section nearer said airway.

5. An attachment for a vacuum cleaning system as set forth in claim 4, further comprising:

said forward projection projecting forwardly and away from said transition cowling to provide a generally narrow and flat projection for reaching away from said transition cowling and enabling said vacuum paddle to reach into narrow areas and including an upraised protuberance to allow hand pressure to be exerted upon said attachment.

6. An attachment for a vacuum cleaning system as set forth in claim 1, wherein said circumscribing ridges further comprise:

circumscribing ridges circumscribing said paddle apertures by circumscribing a perimeter of said vacuum paddle such that said circumscribing ridges lift a bottom surface of said vacuum paddle above a flat surface in contact with said circumscribing ridges.

7. An attachment for a vacuum cleaning system as set forth in claim 1, further comprising:

said paddle apertures increasing in cross-section as travel is made across said vacuum paddle from said point of attachment to a distal end of said vacuum paddle so that more equal volumes of air pass through each paddle aperture.

8. An attachment for a vacuum cleaning system, comprising:

a vacuum paddle attachable to a vacuum system at a point of attachment, said vacuum paddle defining paddle apertures through which air may flow, said vacuum paddle defining an interior plenum space coupled to said paddle apertures;

said paddle apertures increasing in cross-section as travel is made across said vacuum paddle from said point of attachment to a distal end of said vacuum paddle so that more equal volumes of air pass through each paddle aperture;

said vacuum paddle having a generally flat and narrow forward projection generally defining a plane for reaching away from said point of attachment and enabling said vacuum paddle to reach into narrow areas;

said point of attachment including a hollow projection defining an airway and coupleable to the vacuum cleaning system, said hollow projection being generally parallel to but offset from said plane;

a transition cowling defining a mediating plenum coupled on a first side to said vacuum paddle and on a second side to said projection, said mediating plenum in communication with said interior plenum and said airway, said mediating plenum having a larger cross-section nearer said interior plenum and having a narrower cross-section nearer said airway;

said forward projection projecting forwardly and away from said transition cowling to provide a generally narrow and flat projection for reaching away from said transition cowling and enabling said vacuum paddle to reach into narrow areas;

circumscribing ridges circumscribing said paddle apertures by circumscribing a perimeter of said vacuum paddle such that said circumscribing ridges lift a bottom surface of said vacuum paddle above a flat surface in contact with said circumscribing ridges, said circumscribing ridges defining valley openings through which air may flow when said vacuum paddle is placed against a flat surface to ensure air flow to said paddle apertures and to prevent said vacuum paddle from becoming attached to said flat surface by vacuum pressure; and an abrasive pad removably coupleable to said vacuum paddle, said abrasive pad defining pad pores and passageways communicating to said paddle apertures so that said abrasive pad covers said paddle apertures; whereby said vacuum paddle enables better vacuuming of very fine particles.

9. A method for removing particulate matter adhering to a surface, the steps comprising:

providing an abrader coupled to a vacuum system, said abrader having a projecting paddle-like extension for fitting into narrow spaces the undersurface of which is fitted with a porous releasably secured abrasive pad;

abrading the surface with said abrader to release the particulate matter by dislodging it from the surface;

vacuuming said dislodged particulate matter to prevent said matter from dispersing to provide vacuumed particles; and trapping said vacuum particles for disposal; whereby surfaces may be cleaned of the particulate matter adhering to the surface;

wherein the step of providing an abrader further comprises:

providing a vacuum paddle attachable to a vacuum system at a point of attachment, said vacuum paddle defining paddle apertures through which air may flow, said vacuum paddle defining an interior plenum space coupled to said paddle apertures;

said vacuum paddle having a generally flat and narrow forward projection for reaching away from said point of attachment and enabling said vacuum paddle to reach into narrow areas; and circumscribing ridges circumscribing said paddle apertures and defining valley openings through which air may flow when said vacuum paddle is placed against a flat surface to ensure air flow to said paddle apertures and to prevent said vacuum paddle from becoming attached to said flat surface by vacuum pressure such that said vacuum paddle enables better vacuuming of particles.

10. A method for removing particulate matter adhering to a surface as set forth in claim 9, wherein said point of attachment further comprises:

a hollow projection defining an airway and coupleable to the vacuum cleaning system.

11. A method for removing particulate matter adhering to a surface as set forth in claim 10, further comprising:

said vacuum paddle generally defining a plane;

said hollow projection being generally parallel to but offset from said plane.

12. A method for removing particulate matter adhering to a surface as set forth in claim 10, further comprising:

a transition cowling defining a mediating plenum coupled on a first side to said vacuum paddle and on a second side to said projection, said mediating plenum in communication with said interior plenum and said airway, said mediating plenum having a larger cross-section nearer said interior plenum and having a narrower cross-section nearer said airway.

13. A method for removing particulate matter adhering to a surface as set forth in claim 12, further comprising:

said forward projection projecting forwardly and away from said transition cowling to provide a generally narrow and flat projection for reaching away from said transition cowling and enabling said vacuum paddle to reach into narrow areas.

14. A method for removing particulate matter adhering to a surface as set forth in claim 9, wherein said circumscribing ridges further comprise:

circumscribing ridges circumscribing said paddle apertures by circumscribing a perimeter of said vacuum paddle such that said circumscribing ridges lift a bottom surface of said vacuum paddle above a flat surface in contact with said circumscribing ridges.

15. A method for removing particulate matter adhering to a surface as set forth in claim 12, further comprising:

said paddle apertures increasing in cross-section as travel is made across said vacuum paddle from said point of attachment to a distal end of said vacuum paddle so that more equal volumes of air pass through each paddle aperture.

16. A method for removing particulate matter adhering to a surface, the steps comprising:

providing an abrader coupled to a vacuum system, said abrader having a projecting paddle-like extension for fitting into narrow spaces;

said abrader including:

a vacuum paddle attachable to a vacuum system at a point of attachment, said vacuum paddle defining paddle apertures through which air may flow, said vacuum paddle defining an interior plenum space coupled to said paddle apertures;

said paddle apertures increasing in cross-section as travel is made across said vacuum paddle from said point of attachment to a distal end of said vacuum paddle so that more equal volumes of air pass through each paddle aperture;

said vacuum paddle having a generally flat and narrow forward projection generally defining a plane for reaching away from said point of attachment and enabling said vacuum paddle to reach into narrow areas;

said point of attachment including a hollow projection defining an airway and coupleable to the vacuum cleaning system, said hollow projection being generally parallel to but offset from said plane;

a transition cowling defining a mediating plenum coupled on a first side to said vacuum paddle and on a second side to said projection, said mediating plenum in communication with said interior plenum and said airway, said mediating plenum having a larger cross-section nearer said interior plenum and having a narrower cross-section nearer said airway;

said forward projection projecting forwardly and away from said transition cowling to provide a generally narrow and flat projection for reaching away from said transition cowling and enabling said vacuum paddle to reach into narrow areas;

circumscribing ridges circumscribing said paddle apertures by circumscribing a perimeter of said vacuum paddle such that said circumscribing ridges lift a bottom surface of said vacuum paddle above a flat surface in contact with said circumscribing ridges, said circumscribing ridges defining valley openings through which air may flow when said vacuum paddle is placed against a flat surface to ensure air flow to said paddle apertures and to prevent said vacuum paddle from becoming attached to said flat surface by vacuum pressure; and abrading the surface with said abrader to release the particulate matter by dislodging it from the surface;

vacuuming said dislodged particulate matter to prevent said matter from dispersing to provide vacuumed particles; and trapping said vacuum particles for disposal; whereby surfaces may be cleaned of the particulate matter adhering to the surface.

* * * * *